United States Patent
Hayashi

(10) Patent No.: US 8,636,663 B2
(45) Date of Patent: Jan. 28, 2014

(54) ULTRASONIC DIAGNOSTIC APPARATUS AND SOUND SPEED CORRECTION METHOD

(75) Inventor: Tatsuya Hayashi, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 13/381,133

(22) PCT Filed: Jun. 23, 2010

(86) PCT No.: PCT/JP2010/060617
§ 371 (c)(1),
(2), (4) Date: Dec. 28, 2011

(87) PCT Pub. No.: WO2011/001867
PCT Pub. Date: Jan. 6, 2011

(65) Prior Publication Data
US 2012/0101385 A1 Apr. 26, 2012

(30) Foreign Application Priority Data
Jun. 29, 2009 (JP) .................................. 2009-153217

(51) Int. Cl.
*A61B 8/00* (2006.01)
(52) U.S. Cl.
USPC .......................................... 600/437; 382/128
(58) Field of Classification Search
USPC ........................... 600/437–469; 382/128–132
See application file for complete search history.

(56) References Cited

U.S. PATENT DOCUMENTS

| 7,029,445 B2 * | 4/2006 | Shinomura et al. | 600/443 |
| 2005/0075570 A1 * | 4/2005 | Shinomura et al. | 600/459 |
| 2005/0148874 A1 * | 7/2005 | Brock-Fisher et al. | 600/447 |

FOREIGN PATENT DOCUMENTS

| JP | 5-329159 | 12/1993 |
| JP | 2001-187053 | 7/2001 |
| JP | 2002-209887 | 7/2002 |
| JP | 2003-010180 | 1/2003 |
| JP | 2008-264531 | 11/2008 |
| JP | 2009-089940 | 4/2009 |
| JP | 2009-090104 | 4/2009 |

OTHER PUBLICATIONS

International Search Report for PCT International Application No. PCT/2010/060617, mailed on Sep. 14, 2010.

\* cited by examiner

*Primary Examiner* — Sanjay Cattungal
(74) *Attorney, Agent, or Firm* — Brundidge & Stanger, P.C.

(57) ABSTRACT

In order to provide an ultrasonic diagnostic apparatus and a sound speed correction method capable of performing sound speed correction without affecting real-time efficiency, the present invention is characterized in that a reference sound speed image signal is acquired by setting a reference sound speed and a different sound speed image signal is acquired by setting a different sound speed from the reference sound speed and that sound speed correction information is acquired by correcting reference sound speed information based on the reference sound speed image signal using different items of sound speed information based on the different sound speed image signal.

14 Claims, 4 Drawing Sheets

ULTRASONIC DIAGNOSTIC APPARATUS AND SOUND SPEED CORRECTION METHOD

TECHNICAL FIELD

The present invention relates to an ultrasonic diagnostic apparatus and in particular, to an ultrasonic diagnostic apparatus capable of visualizing a high-definition ultrasonic image without depending on the diagnostic part and subject-specific setting conditions.

BACKGROUND ART

The propagation speed (simply referred to as "sound speed") of an ultrasonic wave differs with the diagnostic target part of the subject. In an ultrasonic diagnostic apparatus in the related art, an examiner, such as a doctor or a clinical laboratory technician, can set the sound speed for every target part.

In addition, even if the target part (for example, the liver) is the same, there is a problem in that the sound speed of a received ultrasonic wave in the case of a subject suffering from liver cirrhosis is faster than that in the case of a healthy subject.

Therefore, in PTL 1, a transmission focus generating circuit performs transmission focusing according to the transmission focus pattern which is sequentially selected by a focus pattern selection circuit. A receiving focus generating circuit performs receiving focusing for an echo signal according to the receiving focus pattern corresponding to the transmission focus pattern, and a plurality of image data items with different focus patterns for the same part of the subject are stored in a plurality of memories.

A focus evaluation circuit selects image data in the optimal focus condition by comparing predetermined characteristic amounts of the plurality of image data items stored in the plurality of memories, stores the selected image data in a combination memory, and combines tomographic images. Thus, an ultrasonic diagnostic apparatus has been proposed which always acquires an image in the optimal focus condition regardless of variations in conditions, such as distribution of the sound speed within the subject, and without artificial means.

CITATION LIST

Patent Literature

[PTL 1] JP-A-5-329159

Non Patent Literature

[NPL 1] Recent Medical Imaging Diagnostic Apparatus, Asakura Publishing Co., Ltd. (first printing of first edition, 7.3.2 Characteristics of an image (1) Ultrasonic beam focusing technique)

SUMMARY OF INVENTION

Problem to be Solved by the Invention

In the invention disclosed in PTL 1, however, it is necessary to perform signal transmission by the number of transmission focus patterns in order to generate an optimal image of one frame. This may degrade the frame rate.

It is an object of the present invention to provide an ultrasonic diagnostic apparatus and a sound speed processing method capable of performing sound speed correction without affecting real-time efficiency in the ultrasonic diagnostic apparatus.

Means for Solution to Problem

In order to solve the above-described problem, in the present invention, a reference sound speed image signal is acquired by setting a reference sound speed and a different sound speed image signal is acquired by setting a different sound speed from the reference sound speed, and sound speed correction information is acquired by correcting reference sound speed information based on the reference sound speed image signal using different items of sound speed information based on the different sound speed image signal.

Specifically, an ultrasonic diagnostic apparatus of the present invention includes: a probe which transmits and receives ultrasonic waves to and from a subject; an ultrasonic wave transceiver which drives the probe to transmit ultrasonic waves and also processes a received reflected echo signal and outputs the received reflected echo signal as an image signal; a scan converter which converts the image signal from the ultrasonic wave transceiver into an image signal in a display coordinate system and outputs the image signal; and an image display unit which displays, as an image, the image signal after conversion according to the display coordinate system by the scan converter and is characterized in that the ultrasonic wave transceiver acquires a reference sound speed image signal by setting a reference sound speed and acquires a different sound speed image signal by setting a different sound speed from the reference sound speed and a sound speed correction unit which acquires sound speed correction information by correcting reference sound speed information based on the reference sound speed image signal using different items of sound speed information based on the different sound speed image signal is provided.

In addition, a sound speed correction method of the present invention includes: a step of acquiring a reference sound speed image signal by setting a reference sound speed; a step of acquiring a different sound speed image signal by setting a different sound speed different from the reference sound speed; and a step of acquiring sound speed correction information by correcting reference sound speed information based on the reference sound speed image signal using different items of sound speed information based on the different sound speed image signal.

Advantageous Effects of Invention

According to the present invention, there is provided an ultrasonic diagnostic apparatus and a sound speed processing method capable of performing sound speed correction without affecting real-time efficiency in the ultrasonic diagnostic apparatus.

MODE FOR CARRYING OUT THE INVENTION

Figure 1:
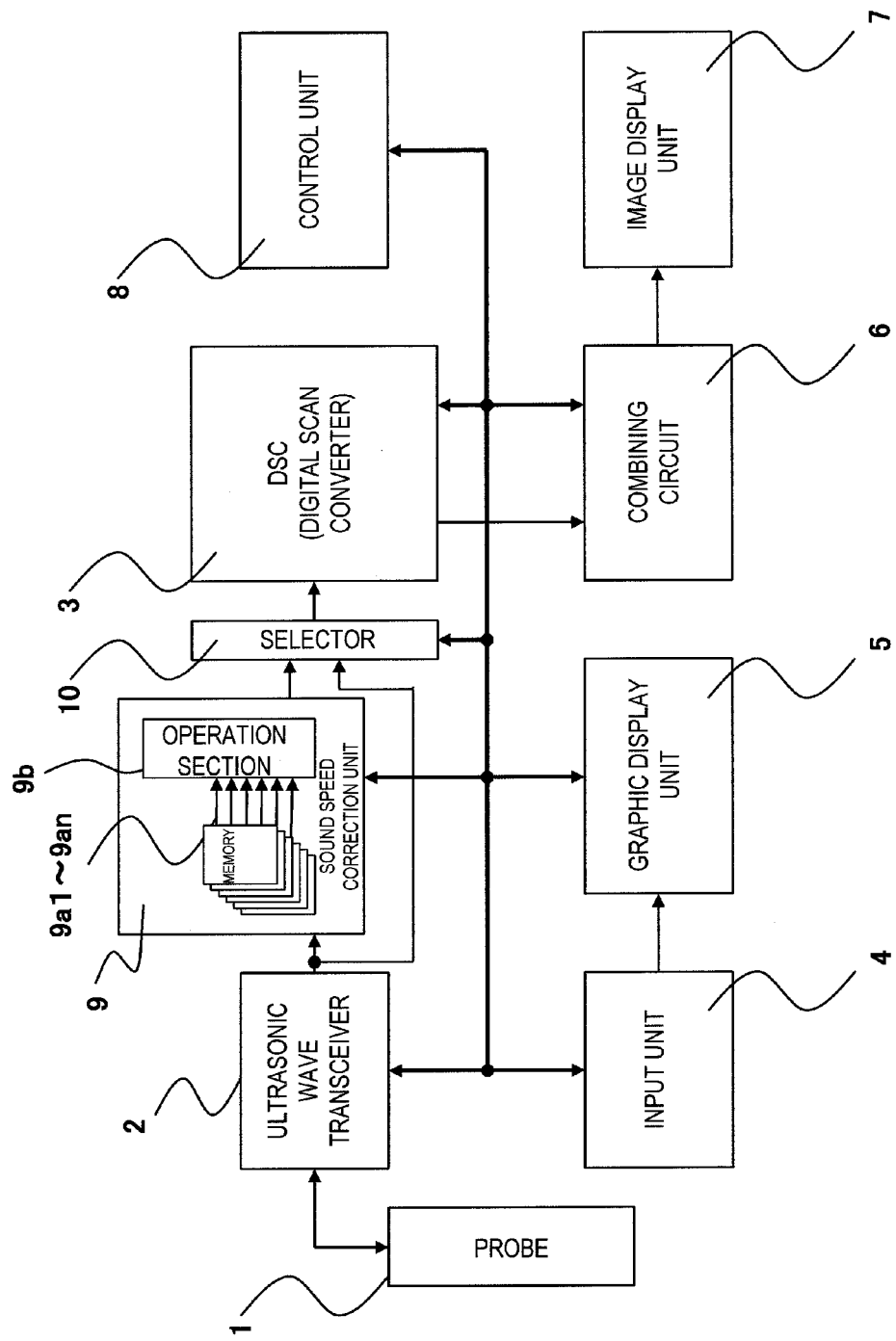
FIG. 1 is a block diagram showing an ultrasonic diagnostic apparatus of a first embodiment of the present invention.

Hereinafter, embodiments of the present invention will be described in detail.

First Embodiment

Hereinafter, a first embodiment of an ultrasonic diagnostic apparatus to which the present invention is applied will be described. Moreover, in the following explanation, the same reference numerals are given to the same functional components, and repeated explanation thereof will be omitted.

In the first embodiment, an example where a selector 10 for switching between inputs of a sound speed correction unit 9 and a scan converter (digital scan converter; DSC) 3 is provided between an ultrasonic wave transceiver 2 and the DSC 3. That is, in the present embodiment, the sound speed correction unit 9 corrects reference sound speed frame data (an aspect of reference sound speed information) based on a reference sound speed image signal using different items of sound speed frame data (an aspect of different items of sound speed information) based on a different sound speed image signal to thereby acquire sound speed correction frame data (an aspect of sound speed correction information).

FIG. 1 is a block diagram showing the configuration of the ultrasonic diagnostic apparatus of the first embodiment of the present invention.

As shown in FIG. 1, the ultrasonic diagnostic apparatus is configured to include an ultrasonic probe (abbreviated as a "probe") 1, the ultrasonic wave transceiver 2, the DSC 3, an input unit 4, a graphic display unit 5, a combining circuit 6, an image display unit 7, and a control unit 8.

The probe 1 transmits and receives ultrasonic waves to and from a diagnostic part in a subject. Types of the probe 1 are mainly divided by the shape of a beam transmitted and received. For example, they are a sector scan-type probe, a linear scan-type probe, a convex scan-type probe, and the like.

The ultrasonic wave transceiver 2 drives the probe 1 to transmit ultrasonic waves and amplifies a received reflected echo signal. Although not shown, the ultrasonic wave transceiver 2 includes a transmitter circuit which transmits a carrier pulse to the probe 1 and generates ultrasonic waves from a built-in oscillator, a receiving amplifier which amplifies a reflected echo signal received by the probe 1, a phase adjusting section which adjusts the phase of the amplified reflected echo signal, and a control circuit thereof.

The DSC 3 writes an image signal from the ultrasonic wave transceiver 2 to an internal memory and also converts the image signal into an image signal in the read display coordinate system and outputs the image signal. The DSC 3 generates image data of one frame by writing the ultrasonic information, which is digitized by an A/D converter in the ultrasonic wave transceiver 2, into a built-in line memory for every plural scanning lines of ultrasonic beams, thereby forming image data of a tomographic image (B-mode image).

The input unit 4 is for inputting a command from an operator with respect to an image or characters displayed on the image display unit 7, which will be described later. For example, the input unit 4 is a pointing device, such as a track ball or a mouse, or a keyboard.

The graphic display unit 5 is for displaying the image information input through the input unit 4, such as a heart rate of a subject or a frequency, as a numeric value or graphically.

The combining circuit 6 combines the image information from the DSC 3 and the graphic display unit 5.

The image display unit 7 is input with the image information from the combining circuit 6 and displays it as an image. For example, the image display unit 7 is a color liquid crystal display, a color CRT, or the like.

The control unit 8 controls the ultrasonic wave transceiver 2, the DSC 3, the input unit 4, the graphic display unit 5, and the combining circuit 6.

The sound speed correction unit 9 includes a plurality of frame memories $9a1$ to $9an$ (n is an arbitrary natural number) and an operation section $9b$ which performs an operation of correcting a frame at the reference sound speed (for example, 1530 m/second in a living body) to a frame at the different sound speed from the reference sound speed. For example, it is possible to acquire images (frame data) of a frame at the reference sound speed and a plurality of frames at the different sound speed from the reference sound speed and to store them in the memories $9a1$ to $9an$.

Here, the memories $9a1$ to $9an$ of the sound speed correction unit 9 are controlled by the control unit 8, and an image at the first sound speed V1 (for example, 1480 m/second which is slower than the reference sound speed) is stored in the memory $9a$ of the memories $9a1$ to $9an$. Similarly, an image at the second sound speed Vc (reference sound speed, for example, 1530 m/second) is stored in the memory $9a2$. In addition, similarly, an image at the third sound speed V2 (for example, 1580 m/second which is faster than the reference sound speed) is stored in the memory $9a3$.

The operation section $9b$ corrects the image at the second sound speed Vc, which is stored in the memories $9a1$ to $9a3$ of the sound speed correction unit 9, using the image at the first sound speed V1 and the image at the third sound speed V2 and outputs a corrected sound speed correction image (frame data).

The selector 10 selects an image before sound speed correction (only the second sound speed Vc) or an image after sound speed correction (output of the operation section $9b$) under control of the control unit 8.

Next, an operation of the present invention configured in this way will be described using FIG. 2.

Figure 2:
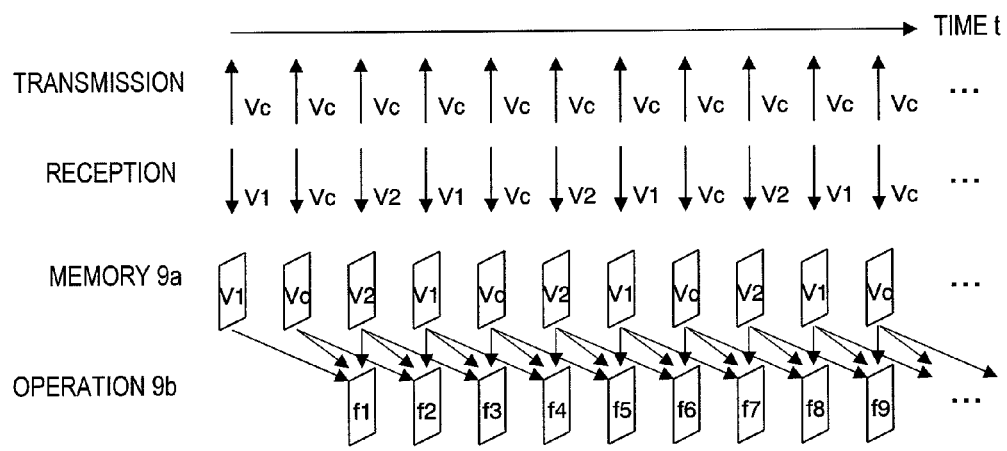
FIG. 2 is a conceptual view showing the scan sequence of the ultrasonic diagnostic apparatus of the first embodiment of the present invention and the flow of storage in a memory.

FIG. 2 is a conceptual view showing the scan sequence of the ultrasonic diagnostic apparatus of the first embodiment of the present invention and the flow of storage in a memory.

Here, an examiner notifies the control unit 8 of a "sound speed correction mode" through the input unit 4. The control unit 8 causes the selector 10 to perform switching from an image before sound speed correction to an image after sound speed correction. The control unit 8 causes the transmitter circuit to transmit a signal while maintaining the sound speed at Vc, and performs signal reception while switching the receiving sound speed Vc of the ultrasonic wave transceiver 2 to V1 or V2 for each frame.

By the control unit 8, the signals received after sound speed switching are stored in the memories $9a1$ and $9a3$. The image at the first sound speed V1 is stored in the memory $9a1$, the image at the second sound speed Vc is stored in the memory $9a2$, and the image at the third sound speed V2 is stored in the memory $9a3$. An image received at the reference sound speed is stored in one frame of the memories $9a1$ to $9a3$. The operation section $9b$ forms a sound speed correction image by performing a correction operation between the image received at the reference sound speed Vc and the signals received at the sound speeds V1 and V2.

FIG. 2 is a view of the scan sequence according to the present invention. This drawing shows a state where images at the reference sound speed Vc and two kinds of different sound speeds V1 and V2 are formed. An ultrasonic wave transmitted at the sound speed Vc is phase-adjusted to V1 by the ultrasonic wave transceiver 2 at the time of signal reception, thereby forming an image of one frame.

Then, the ultrasonic wave is transmitted at the same sound speed Vc and phase-adjusted to Vc at the time of signal reception, thereby forming an image of one frame. Then, the ultrasonic wave is transmitted at the same sound speed Vc and phase-adjusted to V2 at the time of signal reception, thereby forming an image of one frame. The operation section 9b forms one image f1 from the images obtained by three frames of the sound speed V1, Vc, and V2.

In the next frame, the ultrasonic wave is received again at V1, and one image f2 is formed from the images obtained by three frames of the sound speed Vc, V2, and V1. Such an operation of forming a received image is repeated sequentially.

A phase adjusting method according to the set sound speed is disclosed in NPL 1, for example. Accordingly, since this can be used, detailed explanation thereof will be omitted herein.

Figure 3A:
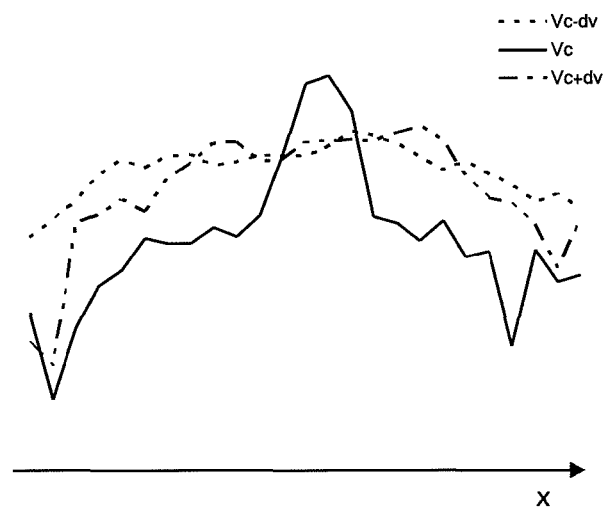
FIG. 3A plots the brightness profile of the brightness of the ultrasonic diagnostic apparatus of the present invention at the reference sound speed and the different sound speed.

Next, the operation of the operation section 9b will be described through an example in order to show the effect of the present invention. FIG. 3A plots the brightness of a given one-dimensional coordinate at the time of capturing a phantom simulating a living body at the reference sound speed Vc and two kinds of different sound speed (V1) Vc−dv and (V2) Vc+dv and imaging it. These images are assumed to be stored in the memory 9a. An image acquired at the sound speed Vc−dv is stored in a memory f (x, y, 0), an image acquired at the reference sound speed Vc is stored in a memory f (x, y, 1), and an image acquired at the sound speed Vc+dv is stored in a memory f (x, y, 2).

Here, (x, y) indicates space coordinates. For example, an operation of an output image g(x, y) is exemplified as a calculation expression of Expression (1).

$$avr(x, y) = \{f(x, y, 0) + f(x, y, 1) + f(x, y, 2)\}/3 \quad \text{Expression (1)}$$

If $f(x, y, 1) > avr(x, y)$ then $g(x, y) = f(x, y, 1) + \alpha * \text{MAX}\{$ $f(x, y, 0) - avr(x, y),$ $f(x, y, 1) - avr(x, y),$ $f(x, y, 2) - avr(x, y)$ $\}$ else $g(x, y) = f(x, y, 1) + \alpha * \text{MIN}\{$ $f(x, y, 0) - avr(x, y),$ $f(x, y, 1) - avr(x, y),$ $f(x, y, 2) - avr(x, y)$ $\}$ Here, $\alpha$ is a coefficient which determines f(x, y, 1) of an output image, that is, the degree of correction of an image acquired at the reference sound speed, MAX( ) is a function for calculating the maximum value, and MIN( ) is a function for calculating the minimum value.

Figure 3B:
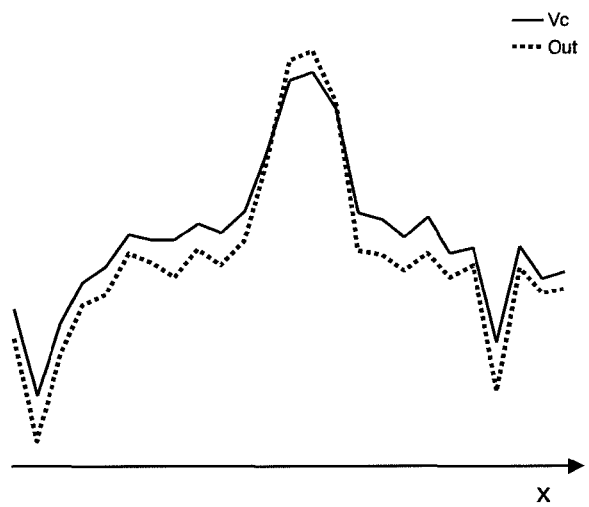
FIG. 3B plots the brightness profile of the brightness of the ultrasonic diagnostic apparatus of the present invention at the reference sound speed and the selector output.

FIG. 3B plots the brightness of the one-dimensional coordinate at the time of outputting on the basis of this calculation and performing imaging. In the image corrected for the reference sound speed Vc, it can be seen that the edge is emphasized and the spatial resolution is improved.

In addition, although the sound speed correction unit 9 is provided before the DSC 3 in the first embodiment, the sound speed correction unit 9 may be located after the DSC 3. In this case, the sound speed correction unit 9 corrects a reference sound speed image (another aspect of the reference sound speed information) based on a reference sound speed image signal using different sound speed images (another aspect of different items of the sound speed information) based on a different sound speed image signal to thereby acquire a sound speed correction image (another aspect of the sound speed correction information). The same effect can also be obtained in this embodiment, and the memory capacity prepared in the memories 9a1 to 9an can be reduced since the converted display image is stored. Therefore, the circuit size of the sound speed correction unit 9 can be reduced.

In the present embodiment, it is not possible to output an image in the first two frames, but it is possible to output an image whenever one frame is received thereafter. Therefore, original real-time efficiency of the ultrasonic diagnostic apparatus is not degraded.

Second Embodiment

A second embodiment is an example where a phase adjusting processing is performed at the reference sound speed and different sound speed in one transmission and reception and the result is stored in a memory.

Figure 4:
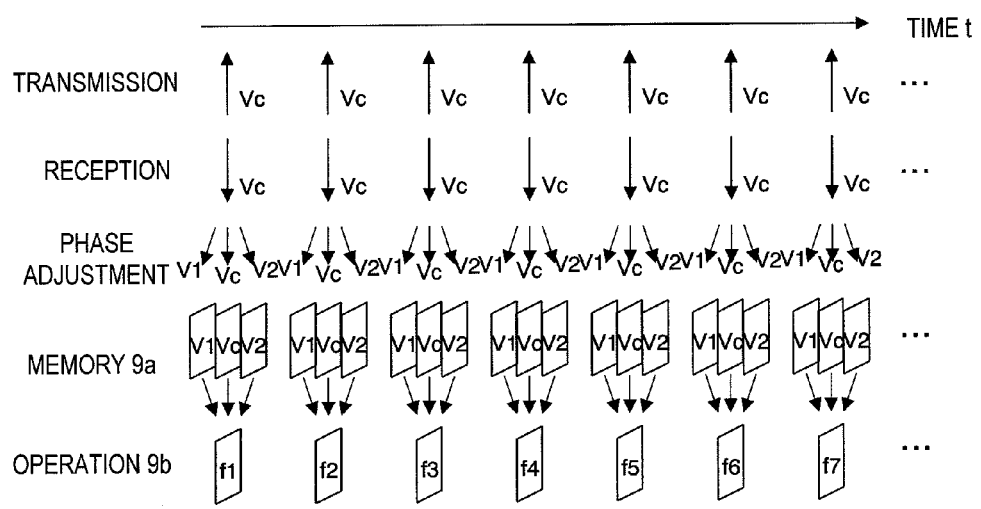
FIG. 4 is a conceptual view showing the scan sequence of the ultrasonic diagnostic apparatus of a second embodiment of the present invention and the flow of storage in a memory.

FIG. 4 is a conceptual view showing the scan sequence of the ultrasonic diagnostic apparatus of the second embodiment of the present invention and the flow of storage in a memory.

In the embodiment shown in FIG. 4, a signal is received at the sound speed Vc and the phase is adjusted at the sound speed of V1, Vc, and V2 by the phase adjusting section of the ultrasonic wave transceiver 2. According to the present embodiment, transmission and visualization of a correction image are performed in the same sequence. Therefore, even in a part of an object with large movement, for example, in the heart, the occurrence of an error due to the time difference is reduced. As a result, correction can be performed with higher accuracy. In addition, it is possible to form an image without wasting the first several frames.

Moreover, in FIG. 2, an image is formed with three frames of the reference sound speed Vc and the two kinds of different sound speeds V1 and V2. However, an image may also be formed with five or seven frames by increasing the number of sound speeds different from the reference sound speed Vc, for example. If the number of different sound speeds is increased, it is possible to realize more accurate sound speed correction.

In addition, when it can be apparently said that the sound speed is increased or decreased according to the examined organ of the subject, it is also possible to use the reference sound speed and one different sound speed. If the reference sound speed and one different sound speed are used, the circuit size of the memory 9a can be reduced.

As is apparent from the above explanation, according to the ultrasonic diagnostic apparatus of the present embodiment, sound speed correction is automatically performed in the ultrasonic diagnostic apparatus. As a result, it is possible to provide an ultrasonic tomographic image with high spatial resolution without depending on a patient and a target part.

In addition, although some preferred embodiments of the ultrasonic diagnostic apparatus related to the present invention have been described with reference to the drawings, the present invention is not limited to such examples. It is apparent to those skilled in the art that various changes and modifications can be made within the range of the technical idea disclosed in this description, and it should be understood that they naturally also belong to the technical range of the present invention.

REFERENCE SIGNS LIST

9: sound speed correction unit
9a: memory
9b: operation section

The invention claimed is:

1. An ultrasonic diagnostic apparatus comprising:
a probe which transmits and receives ultrasonic waves to and from a subject;
an ultrasonic wave transceiver which drives the probe to transmit ultrasonic waves and also processes adjusting of phases of a received reflected echo signal, at a sound velocity having a predetermined value, and outputs the received reflected echo signal as an image signal;
a scan converter which converts the image signal from the ultrasonic wave transceiver into an image signal in a display coordinate system and outputs the image signal; and
an image display unit which displays, as an image, the image signal after conversion according to the display coordinate system by the scan converter,
wherein the ultrasonic wave transceiver acquires a reference sound speed image signal by setting a reference sound speed and acquires a different sound speed image signal by setting a different sound speed from the reference sound speed; and
a correction unit which acquires a corrected image signal by correcting a first each pixel value of an image signal obtained at a sound velocity having a reference value by using a second each pixel value of an image signal obtained at a sound velocity different from the sound velocity having the reference value, respectively,
wherein the scan converter converts the corrected image signal into an image signal in a display coordinate system, and
wherein the image display unit displays an image, according to the display coordinate system, by using the image signal after conversion by the scan converter.

2. The ultrasonic diagnostic apparatus according to claim 1, wherein the sound speed correction unit is disposed between the ultrasonic wave transceiver and the scan converter, and acquires sound speed correction frame data by correcting reference sound speed frame data based on the reference sound speed image signal using different items of sound speed frame data based on the different sound speed image signal.

3. The ultrasonic diagnostic apparatus according to claim 1, wherein the sound speed correction unit is disposed between the scan converter and the image display unit, and acquires a sound speed correction image by correcting a reference sound speed image based on the reference sound speed image signal using a different sound speed image based on the different sound speed image signal.

4. The ultrasonic diagnostic apparatus according to claim 1, wherein the ultrasonic wave transceiver acquires the reference sound speed image signal and the different sound speed image signal sequentially at the time of signal reception.

5. The ultrasonic diagnostic apparatus according to claim 1, wherein the ultrasonic wave transceiver sets the reference sound speed and transmits ultrasonic waves through the probe.

6. The ultrasonic diagnostic apparatus according to claim 1, wherein the ultrasonic wave transceiver sets the different sound speed and adjusts a phase of the received reflected echo signal.

7. The ultrasonic diagnostic apparatus according to claim 1,
wherein the ultrasonic wave transceiver acquires a first different sound speed image signal by setting a sound speed slower than the reference sound speed and acquires a second different sound speed image signal by setting a sound speed faster than the reference sound speed, and
wherein the sound speed correction unit acquires sound speed correction information by correcting the reference sound speed information by correcting and using the first different sound speed image information based on the first different sound speed image signal and second different sound speed image information based on the second different sound speed image signal.

8. The ultrasonic diagnostic apparatus according to claim 1, wherein the ultrasonic wave transceiver acquires the reference sound speed image signal by setting the reference sound speed at the time of signal reception and performs phase adjustment processing on the reference sound speed image signal by setting the reference sound speed and the different sound speed for the acquired reference sound speed image signal.

9. The ultrasonic diagnostic apparatus according to claim 1, further comprising:
an input unit which receives an input of sound speed,
wherein the ultrasonic wave transceiver acquires the reference sound speed image signal or the different sound speed image signal according to the input sound speed.

10. An ultrasonic diagnostic apparatus according to claim 1, wherein a position of the first each pixel value in the image is the same as a position of the second each pixel value in the image.

11. A sound speed correction method performed by an ultrasonic diagnostic apparatus, comprising:
a step of acquiring a reference sound speed image signal by setting a reference sound speed;
a step of acquiring a different sound speed image signal by setting a different sound speed from the reference sound speed; and
a step of acquiring a corrected image signal by correcting a first each pixel value of an image signal obtained at a sound velocity having a reference value by using a second each pixel value of an image signal obtained at a sound velocity different from the sound velocity having the reference value, respectively,
wherein the scan converter converts the corrected image signal into an image signal in a display coordinate system, and
wherein the image display unit displays an image, according to the display coordinate system, by using the image signal after conversion by the scan converter.

12. The sound speed correction method according to claim 11,
wherein in the step of acquiring the different sound speed image signal, a first different sound speed image signal is acquired by setting a sound speed slower than the reference sound speed and a second different sound speed image signal is acquired by setting a sound speed faster than the reference sound speed, and wherein in the step of acquiring the sound speed correction information, sound speed correction information is acquired by correcting and using the first different sound speed image information based on the first different sound speed image signal and second different sound speed image information based on the second different sound speed image signal.

13. The sound speed correction method according to claim 11, further comprising:

a step of acquiring reference sound speed frame data as the reference sound speed information on the basis of the reference sound speed image signal; and a step of acquiring different sound speed frame data as the different sound speed information on the basis of the different sound speed image signal, wherein in the step of acquiring the sound speed correction information, sound speed correction frame data is acquired by correcting the reference sound speed frame data using the different sound speed frame data.

14. The sound speed correction method according to claim 11, further comprising:

a step of acquiring a reference sound speed image as the reference sound speed information on the basis of the reference sound speed image signal; and a step of acquiring a different sound speed image as the different sound speed information on the basis of the different sound speed image signal, wherein in the step of acquiring the sound speed correction information, a sound speed correction image is acquired by correcting the reference sound speed image using the different sound speed image.

* * * * *